US00PP08211P

United States Patent [19]

Janzen

[11] Patent Number: Plant 8,211

[45] Date of Patent: Apr. 27, 1993

[54] "ROYAL LADY" PEACH TREE

[76] Inventor: Franklin J. Janzen, 16321 E. Floral Ave., Reedley, Calif. 93654

[21] Appl. No.: 697,677

[22] Filed: May 9, 1991

[51] Int. Cl.[5] ..... A01H 5/00

[52] U.S. Cl. ..... Plt./43.2

[58] Field of Search ..... Plt. 43, 43.2

[56] References Cited

U.S. PATENT DOCUMENTS

P.P. 4,399 3/1979 Merrill ..... Plt. 43

P.P. 7,169 2/1990 Lewis ..... Plt. 43

*Primary Examiner*—James R. Feyrer

*Attorney, Agent, or Firm*—Worrel & Worrel

[57] ABSTRACT

A new and distinct variety of peach tree which is somewhat remotely similar to the "Elegant Lady" peach tree (U.S. Plant Pat. No. 4,399), but from which it is distinguished by producing fruit which is mature for harvesting and shipment approximately Jul. 20 to Aug. 2 in the central San Joaquin Valley of California, the fruit being freestone by nature having a round shape and which further exhibits a full red coloration in shades of light red to dark red and a pleasing, very crisp yellow flesh.

1 Drawing Sheet

BACKGROUND OF THE NEW VARIETY

The present invention relates to a new and distinct variety of peach tree which will hereinafter be denominated varietally as "Royal Lady" and, more particularly, to a peach tree which produces freestone fruit which is mature for commercial harvesting and shipment approximately Jul. 20 to Aug. 2 in the San Joaquin Valley of central California, and which is further distinguished by a large, bright and attractive orange-red skin coloration which is firm and crisp and which has noteworthy shipping and handling characteristics.

The discovery of new varieties of fruit trees having significant commercial potential is an event having considerable, and possibly enduring, benefits in commercial markets. Such commercial markets are very receptive, in particular, to new varieties of peach trees producing fruit which, in general, possesses excellent market acceptance. Where such new varieties of peach tree produce fruit which is larger, or, having higher coloration or being earlier or later ripening, or having better flavor, or any of a myriad of other attributes when compared with its most nearly similar competing varieties, the new variety possesses considerable potential value in the marketplace. The peach tree of the instant invention is just such a new variety of peach tree.

ORIGIN AND ASEXUAL REPRODUCTION OF THE NEW VARIETY

The present variety of peach tree hereof was discovered by the inventor in an orchard of "Elegant Lady" peach trees of the inventor located in Reedley in the San Joaquin Valley of central California. The new variety was discovered on Jul. 8, 1989 as a sport of an "Elegant Lady" peach tree in the orchard. The sport of the new variety consistently bore fruit ripening two weeks later than the fruit of the "Elegant Lady" peach trees in the same orchard.

The new variety was asexually reproduced at the direction of the inventor in Dec., 1989 by dormant budding in the same orchard in which the sport of the parent tree was discovered. The invention observed the progeny through the next successive growing seasons and confirmed that the characteristics thereof were identical to those of the parent. More specifically, the fruit produced by the asexually reproduced trees of the new variety were observed in 1991 with the first picking of the fruit taking place on Aug. 1, 1991. In contrast, the first picking of fruit of the "Elegant Lady" peach trees in the same orchard was on Jul. 13, 1991. In 1992, the first picking of fruit of the new variety was on Jul. 18, 1992 while that of the "Elegant Lady" peach trees was Jul. 3, 1992.

SUMMARY OF THE NEW VARIETY

The "Royal Lady" peach tree is characterized by producing large freestone fruit of a light orange-red to a darker red coloration, including a flesh color of an amber-yellow. The fruit has an excellent flavor and the flesh has a firm and crisp texture at commercial maturity. The fruit produced by the "Royal Lady" peach tree is ripe for commercial harvesting and shipment approximately Jul. 20 to Aug. 2 in the San Joaquin Valley of central California. The new variety is perhaps most closely similar to the "Elegant Lady" peach tree (U.S. Plant Pat. No. 4,399), but is distinguishable therefrom and is characterized as to novelty by producing a high quality, high color, productive, mid season peach, maturing in the third to last week of July.

In comparison with the fruit of the "Elegant Lady" peach tree, the new variety is two weeks later in maturity with harvest beginning Jul. 20, in 1990. In contrast, the "Elegant Lady" peach tree has a harvest date of Jul. 6 in 1990 in the San Joaquin Valley of Central California.

BRIEF DESCRIPTION OF THE DRAWING

The accompanying drawing is a color photograph showing fruit of the new variety including a first in bottom plan view showing the apex end thereof; a second in top plan view showing the stem cavity thereof; a third in side elevation; a fourth sectioned in the sutre plane to expose the flesh thereof and showing the pit well; and a fifth sectioned in the suture plane to expose the flesh thereof and showing the stone in position in the pit well; and foliage typical of the new variety of peach tree.

DETAILED DESCRIPTION

Referring more specifically to the pomological details of this new and distinct variety of peach tree, the following has been observed under the ecological conditions prevailing at the nursery of origin which is located in Reedley, Calif. All major color code designations are by reference to the *Dictionary of Color,* by Maerz and Paul, Second Edition, 1950.

TREE

Generally: Upright, spreading with density and eventual form determined by pruning.

*Productivity.*—Productive. The tree is hardy under growing conditions typical for the San Joaquin Valley of central California.

*Regularity of Bearing.—Regular.*

Trunk:

Size.—Diameter in relation to length— Average.

*Surface texture.*—Average.

*Color.*—Grayish-brown (8-H-10).

*Lenticels.—Numbers — Numerous large and narrow lenticels. Color — Lenticels surrounded with medium brown callous tissue (*15A-11).

Branches:

*Size.*—Average thickness.

*Surface texture.*—Smooth.

*Color.*—Brown (7-H-10). Color - Shoots - Light green (19-K-6) and those that are exposed to direct sunlight are often tinged with red.

LEAVES

Size:

*Generally.*—Large.

*Average length.*—18.0 cm (7.086 inches) including the petiole.

*Average width.*—4.2 cm (1.653 inches).

Form:

*Shape.*—Lanceolate.

Tip: Acuminate. Tip is slightly to moderately twisted sideways.

Color:

*Upwardly disposed surface.*—Dark green (24-L-2).

*Downwardly disposed surface.*—Light grey-green (23-J-2).

*Mid vein.*—Light green (19-H-4) on the under side of leaf.

Marginal form: Crenate. Crenations rather broad and shallow. Leaf margins moderately undulate.

Glandular characteristics: Glands are predominantly of reniform type and variable in number. Most often 1 to 3 reniform glands are present on the lower edge of the leaf margin. Additionally, 0 to 3 more glands are present on the leaf petiole. These glands can be either reniform or globose in type. Globose types are usually stalked.

*Gland— Position.*—Alternate.

*Gland— Color.*—Light green (18-K-4) and darkens substantially with age.

*Gland surface.*—Shiny.

Stipules: Most often two moderately long stipules are present subtending the leaf petiole. Stipules are early deciduous.

*Length.*—9 mm (0.354 inches) to 10 mm (0.393 inches).

*Margin.*—Serrate.

*Color.—Yellow-green (*18-k-6).

Petiole:

*Length.*—9.0 mm (0.354 inches) to 11.0 mm (0.433 inches).

*Thickness.*—1.5 mm (0.059 inches).

*Color.*—Light green (20-K-4).

FLOWERS

Flower buds:

*Size.—Medium.*

*Shape.*—Conic.

*Color.*—Medium brown (Laurel Oak 7-J-10).

*Scales.*—Highly pubescent with a light grey pubescence.

Flowers — generally: Small.

Bloom quantity: Abundant. Most commonly two flower buds per node.

Date of bloom: Feb. 26th.

Size: *Diameter.*—23 mm (0.905 inches).

Shape: Non-showy.

Petals: Characteristically rolled inwards, even at full maturity.

*Color.*—Light pink (1-D-1) in the center of the petal, becoming darker near the margins and on the petal claw (1-G-3).

*Number.*—Five.

*Form.*—Ovate.

*Size.*—Average. Length — 14.5 mm (0.570 inches). Width — 9.5 mm (0.374 inches).

Petal claw: Relatively narrow, short and truncate.

Petal margin: Substantially undulate.

Petal apex:

*Generally.*—Rounded.

Pedicel: Medium to slightly short. Length — 2.5 mm (0.098 inches). Thickness — 2.0 mm (0.078 inches). Glabrous.

*Color.*—Light green (18-L-6).

Nectaries:

*Color.*—Bright orange (9-J-9), darkening slightly with age.

Anthers:

*Size.*—Average.

*Color.*—Light tan (9-G-3) ventrally, with red coloration (Pompeian Red 4-J-10) on the dorsal side.

Pollen: Abundant

*Color.—Yellow (*10-L-3).

Stamens: *Length.*—15 mm (0.590 inches) to 16 mm (0.629 inches), slightly shorter than the pistil at full development.

Filament color — Very light pink (1-B-1) when young, darkening to a dark rose (Persian Pink 3-H-4) when fully mature.

Pistil:

*Length.*—19 mm (0.748 inches). Highly pubescent.

*Color.*—Light green (17-J-4). Pollination requirements: Same as for the "Elegant Lady" peach tree.

FRUIT

Maturity when described: Ripe for commercial harvesting and shipment approximately July 20 to August 2 at Reedley, Calif.

Size:

*Generally.*—Uniformity — large.

*Average cheek diameter.*—75 mm (2.952 inches) to 81 mm (3.188 inches.

*Average diameter in the suture plane.*—80 mm (3.149 inches) to 82 mm (3.228 inches).

*Average axial diameter.*—76 mm (2.992 inches) to 83 mm (3.267 inches).

*Form.*—Uniformity — uniform. Symmetry— Symmetrical to a very slightly asymmetrical. Nearly globose in axial aspect with moderately prominent suture. Broadly ovate to nearly globose in lateral aspect.

*Suture.*—Generally — A narrow distinct line from base to apex. The suture usually takes on the color of the underlying blush or ground color in the area surrounding the suture rather than having its own distinct uniform coloration. The suture is smooth, although moderately prominent, with only a slight amount of suture stitching in the mid-suture area.

*Ventural surface.*—Rounded and moderately prominent. Ventral surface is variable and can be slightly lipped or not lipped at all. One side of fruit usually protrudes more than the other.

*Stem cavity.*—Branch imprint is often present in the fruit basal shoulder. Size — Moderate. Form — Narrow oval. Width — 18 mm (0.078 inches) to 22 mm (0.866 inches). Length — 30 mm (1.181 inches) to 34 mm (1.338 inches). Depth — Moderately deep, 14 mm (0.551 inches) to 16 mm (0.629 inches).

*Base.*—Rounded to slightly truncate. Most frequently slightly oblique to the fruit axis.

*Apex.*—Variable, from rounded to moderately pointed.

*Pistil point.*—Apical. A slight depression is present on the ventral suture next to the apex.

*Stem.*—Size — Moderate. Length — 11 mm (0.433 inches) to 13 mm (0.511 inches). Width — 4.0 mm (0.157 inches) to 4.5 mm (0.177 inches). Color — Light green-yellow (19-K-3).

Skin:

*Thickness.*—Average with mild flavor. Tenacious to flesh at commercial maturity but will pull free from flesh at soft ripe maturity.

*Color—blush.*—Bright and attractive. Variable in intensity and amount. Can cover from 60 to 90 percent of the fruit surface. Intensity ranges from a light orange-red (3-I-11) to a darker red (5-K-11) with many degrees intensity variation in between.

*Color.*—Light yellow-amber (10-J-4). Skin surface is clean with only a few light colored dots present, mostly over the apical shoulders.

Tendency to crack.—None observed.

*Pubescence.*—Light, short pubescence.

Flesh:

*Texture.*—Firm and crisp at commercial maturity becoming melting at full maturity.

*Flesh color.*—Uniform in color from beneath the skin up to within 5 mm of the stone cavity. Amber-yellow (11-K-5).

*Surface of pit cavity.*—Stained red (4-K-10) with a few rays of red coloration extending as much as 6 mm (0.236 inches) to 8 mm (0.314 inches) into the flesh. A moderate amount of white callous tissue is present on the surface of the stone cavity.

*Flavor.*—Good to excellent and slightly acidic.

*Aroma.*—Slight, pleasant.

*Fibers.*—Medium to few in number, short in length and tender in texture.

*Ripening.*—*Even.*

*Eating quality.*—Well above average.

Stone:

*Attachment.*—Freestone. Stone pulls free from flesh cleanly with only a few fibers clinging to stone basally.

*Fibers.*—Few, moderately thick, attached basally in grooves and pit.

*Size.*—Generally — Medium. Length — 35 mm (1.377 inches) to 40 mm (1.574 inches). Width — 26 mm (1.023 inches) to 28 mm (1.102 inches). Thickness — 19 mm (0.748 inches) to 22 mm (0.866 inches).

*Form.*—Somewhat irregular but most generally slightly obovate to almost oval.

*Apex.*—Acute in form with a sharp acuminate tip.

*Color.*—Dry — Light brown (14-B-11) with a moderate amount of purple-red staining, especially basally.

*Base.*—Rounded. Base angle variable from quite oblique to the stone axis to at right angle to the axis.

Hilum.—Moderately large and well defined. Hilum is oval in form with a moderately thick, grooved collar.

*Sides.*—Very coarse in form with jagged ridges over the apical shoulders and deep, irregular pits and grooves over the lateral surfaces and basally, Stone sides are equal or only very slightly unequal in size.

*Ventral edge.*—Broad with a series of low irregular wings converging apically. Wings are more distinct in the mid-suture area.

*Dorsal edge.*—Very coarse with two high ridges subtending a deep, wide groove from stone base to above mid-stone. The apical shoulder of the dorsal suture is heavily eroded and forms a concave area just below the apex. The high dorsal ridges are cut by deep grooves in several locations, especially at mid-suture.

*Tendency to split.*—None observed.

Use: Fresh market, dessert type peach with potential for use in local markets and long distance shipping.

Keeping quality: good

Although the new variety of peach tree possesses the described characteristics noted above as a result of the growing conditions prevailing near Reedley in the central part of the San Joaquin Valley of central California, it is to be understood that variations of the usual magnitude and characteristics incident to changes in growing conditions, fertilization, irrigation, pruning, pest control and the like are to be expected.

Having thus described and illustrated my new variety of peach tree, what I claim as new and desire to be secured by Plant Letters Patent is:

1. A new and distinct variety of peach tree substantially as illustrated and described and which was discovered as a sport of the "Elegant Lady" peach tree (U.S. Plant Pat. No. 4,399), but from which it is distinguished and characterized principally as to novelty by producing a freestone fruit which is mature for harvesting and shipment approximately July 20 to August 2 in the San Joaquin Valley of central California, the fruit having from a light orange-red to a darker red coloration, a flesh which is amber-yellow and of a firm and crisp texture with skin tenacious to the flesh at commercial maturity but will pull free from flesh at soft ripe maturity.

* * * * *

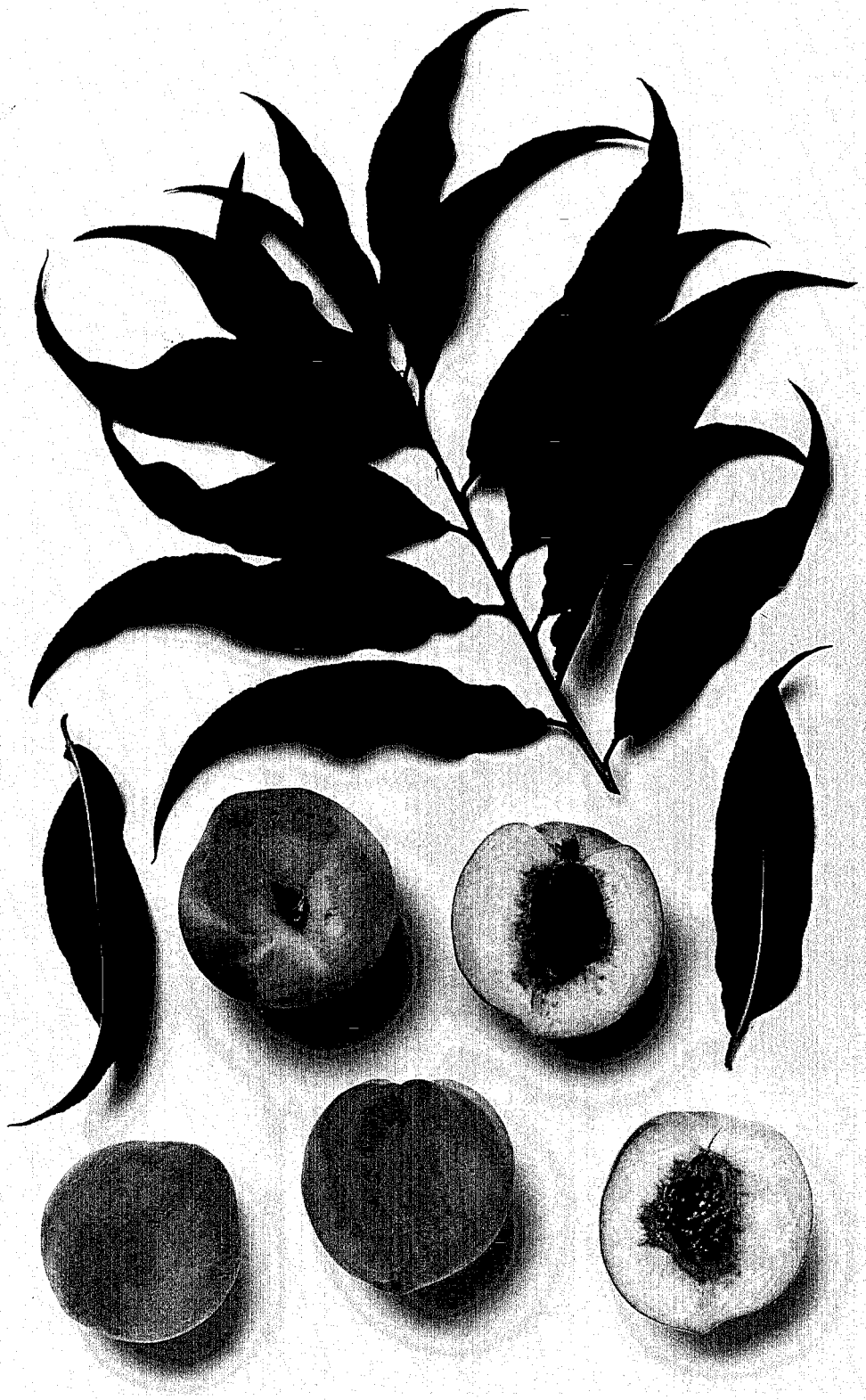

UNITED STATES PATENT AND TRADEMARK OFFICE

CERTIFICATE OF CORRECTION

PATENT NO. : PP: 8,211

DATED : April 27, 1993

INVENTOR(S) : Franklin J. Janzen

It is certified that error appears in the above-identified patent and that said Letters Patent is hereby corrected as shown below:

Column 2, line 31, the "C" in "Central" should be lower case.

Column 2, line 40, delete "sutre" and substitute ---suture---.

Column 3, line 24, delete "(15A-11)" and substitute ---(15-A-11)---.

Column 3, line 67, the "k" in "(18-k-6)" should be upper case.

Column 4, line 66, delete "(3.188 inches." and substitute ---(3.188 inches).---

Column 5, line 3, the "u" in "uniform" should be upper case.

Column 5, line 16, delete "Ventural" and substitute ---Ventral---.

Column 5, line 23, delete "(0.078)" and substitute ---(0.708 inches)---.

Column 5, line 47, delete "Color." and substitute ---Color-Ground---.

Signed and Sealed this

Twenty-eighth Day of December, 1993

*Attest:*

Bruce Lehman

BRUCE LEHMAN

*Attesting Officer*

*Commissioner of Patents and Trademarks*